United States Patent
Newell et al.

(10) Patent No.: US 9,016,113 B2
(45) Date of Patent: Apr. 28, 2015

(54) TESTING DEVICE AND METHOD FOR TESTING SCISSORS

(71) Applicant: Wolff Industries, Inc., Spartanburg, SC (US)

(72) Inventors: Walker Newell, Elizabethtown, IN (US); David Scott Vogel, Columbus, IN (US)

(73) Assignee: Wolff Industries, Inc., Spartanburg, SC (US)

( * ) Notice: Subject to any disclaimer, the term of this patent is extended or adjusted under 35 U.S.C. 154(b) by 311 days.

(21) Appl. No.: 13/742,642

(22) Filed: Jan. 16, 2013

(65) Prior Publication Data

US 2013/0186190 A1    Jul. 25, 2013

Related U.S. Application Data (60) Provisional application No. 61/588,325, filed on Jan. 19, 2012.

(51) Int. Cl.
*B23Q 17/09* (2006.01)
*G01N 19/08* (2006.01)
*G01N 3/58* (2006.01)

(52) U.S. Cl.
CPC . *G01N 19/08* (2013.01); *G01N 3/58* (2013.01)

(58) Field of Classification Search
CPC ............ G01N 3/58; G01N 2203/0053; G01M 99/007
USPC ......................................... 73/104, 839, 865.9
See application file for complete search history.

(56) References Cited

U.S. PATENT DOCUMENTS

| | | | |
|---|---|---|---|
| 3,785,201 A | 1/1974 | Rubio et al. | |
| 3,827,281 A | 8/1974 | Hamel | |
| 4,448,079 A | 5/1984 | Schumacher et al. | |
| 4,691,576 A | 9/1987 | Schleuniger et al. | |
| 4,791,807 A | 12/1988 | Oechsle | |
| 4,864,852 A | 9/1989 | Boone | |
| 4,934,185 A | 6/1990 | Nishiyama et al. | |
| 5,597,649 A | 1/1997 | Sandor et al. | |
| 6,681,622 B1 | 1/2004 | Valentine et al. | |
| 7,694,964 B2 | 4/2010 | Kawasaki et al. | |
| 8,047,069 B2 | 11/2011 | Coulter et al. | |
| 2006/0201237 A1* | 9/2006 | Dowd | 73/104 |

OTHER PUBLICATIONS

CATRA ( Cutlery and Allied Trades Research Association), Scissors cutting performance test machine, Aug. 6 2008, http://www.catra.org/pages/products/sissors/stm.htm and https://www.youtube.com/watch?v=8Tb51yoQJDU.*
Anago Operating & Analysis Software; www.anago.co.nz/sharpness-analyzer/anago-analysis-software/ ; as found Jan. 16, 2013.
Scissors Cutting Performance Test Machine; www.catra.org/pages/products/sissors/stm.htm ; as found Jan. 16, 2013.

* cited by examiner

*Primary Examiner* — John Fitzgerald
*Assistant Examiner* — Truong Phan
(74) *Attorney, Agent, or Firm* — Dority & Manning, P.A.

(57) ABSTRACT

A testing device and method for testing scissors are disclosed. The testing device includes a mount device. The mount device includes a first mount feature for mounting a first grip end of the scissors thereon and a second mount feature movable with respect to the first mount feature for mounting a second grip end of the scissors thereon. The testing device additionally includes a feed device positioned to provide a test media between a first blade and a second blade of the scissors. The testing device further includes a position sensor associated with the mount device for measuring movement of the second grip end, and a load sensor associated with the mount device for measuring a load required for the scissors to cut the test media.

20 Claims, 7 Drawing Sheets

TESTING DEVICE AND METHOD FOR TESTING SCISSORS

TECHNICAL FIELD

The present disclosure relates to testing devices and methods for testing blade sharpness, and more particularly to testing devices and methods for testing scissors.

BACKGROUND

Scissors are utilized in a wide variety of applications, ranging from various uses in the home to uses in manufacturing plants and processing plants. One particular application is scissors is in food processing plants. In these plants, scissors are used to process various particular parts of animals. For example, scissors may be used to trim skin or fat, to separate meat from bone, or to cut meat into separate portions.

One issue that has arisen during the use of scissors in any application, and specifically in food processing applications, is the sharpness of the blades of the scissors. During use, the blades are gradually dulled. Duller blades cause cuts to be inaccurate and imprecise, and can cause injuries to the workers using the scissors. Further, and particularly in food processing applications which can require repetitive use, the increased pressure required for cutting due to dulling of the blades can cause musculoskeletal injuries, such as carpal tunnel syndrome.

Thus, methods and apparatus for monitoring the sharpness of the blades of scissors are desired in the art. However, currently known testing apparatus have a variety of disadvantages. For example, currently known testing apparatus monitor only the peak force required for cutting by scissors, and provide no information regarding increases or decreases in force throughout cutting or where along the blades of the scissors the peak force requirements occur.

In view of the above, an improved testing device and method for testing scissors would be desired in the art. For example, an improved testing device and method that provide improved force and position information for the scissors blades during testing would be particularly advantageous.

SUMMARY

Aspects and advantages of the invention will be set forth in part in the following description, or may be obvious from the description, or may be learned through practice of the invention.

In one embodiment, a testing device for testing scissors is disclosed. The testing device includes a mount device. The mount device includes a first mount feature for mounting a first grip end of the scissors thereon and a second mount feature movable with respect to the first mount feature for mounting a second grip end of the scissors thereon. The testing device additionally includes a feed device positioned to provide a test media between a first blade and a second blade of the scissors. The testing device further includes a position sensor associated with the mount device for measuring movement of the second grip end, and a load sensor associated with the mount device for measuring a load required for the scissors to cut the test media.

In another embodiment, a method for testing scissors is disclosed. The method includes receiving a signal associated with a load measurement from a load sensor during cutting of a test media by the scissors, and receiving a signal associated with a movement measurement from a position sensor during cutting of the test media by the scissors. The method further includes outputting a correlation between load required for the scissors to cut the test media and location along a first and second blade of the scissors where cutting of the test media occurs.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

In general, the present disclosure is directed to a testing device. The testing device is utilized for testing scissors, and specifically for testing the sharpness of the scissors blades. This is generally accomplished by determining the amount of force that is required for the blades to cut through a test media. As the blades become blunter (less sharp), the force may generally increase. The testing device can be utilized to determine the force of scissors, which beneficially allows for determinations to then be made regarding sharpening or replacing the scissors. Further, the testing device advantageously correlates the force required for cutting the test media with the cutting location along the blades of the scissors. This allows peaks and/or valleys in the required force can be observed and located, and better, more informed determinations to be made regarding sharpening or replacing of the scissors.

Testing devices according to the present disclosure may be utilized, and are beneficial, in any suitable environment where scissors are utilized. Further, it should be understood that the term "scissors" includes any suitable cutting apparatus having two blades, at least one of which is movable towards the other such that the cutting device is capable of cutting a test media therebetween. One exemplary use of a testing device according to the present disclosure is in a food processing plant, for testing the sharpness of scissors utilized for processing animals. For example, the testing device can be utilized to test selected scissors at selected time intervals to determine the sharpness of those as well as similarly situated scissors. The scissors can then be sharpened or replaced as needed. Use of testing devices in such environments can reduce the risk of injuries, including cutting or stabbing injuries as well as the development of musculoskeletal injuries, such as carpal tunnel syndrome.

Referring now to FIGS. 1 through 6, embodiments of a testing device 10 according to the present disclosure are shown. A testing device 10 according to the present disclosure may be utilized to test scissors 12, exemplary embodiments of which are shown. Scissors 12 may include a first grip end 16 and a first blade 18, which may be connected as shown. For example, the blade 18 may extend from the grip end 16, which may in some embodiments be molded around an end of the blade 18. Scissors 12 may additionally include a second grip end 20 and a second blade 22, which may be similarly connected. The first grip end 16 and first blade 18 may be fastened to the second grip end 20 and second blade 22, such as pivotally fastened at a pivot point 24 on the blades 18 and 22. The blades 18 and 22 may face each other, so that cutting may occur between the blades 18 and 22 when they are moved towards one another, such as through pivoting about the pivot point 24. Thus, the scissors 12 may alternate between an open position with the blades 18 and 22 spaced apart from each other and a closed position with the blades 18 and 22 overlapping.

Figure 1:
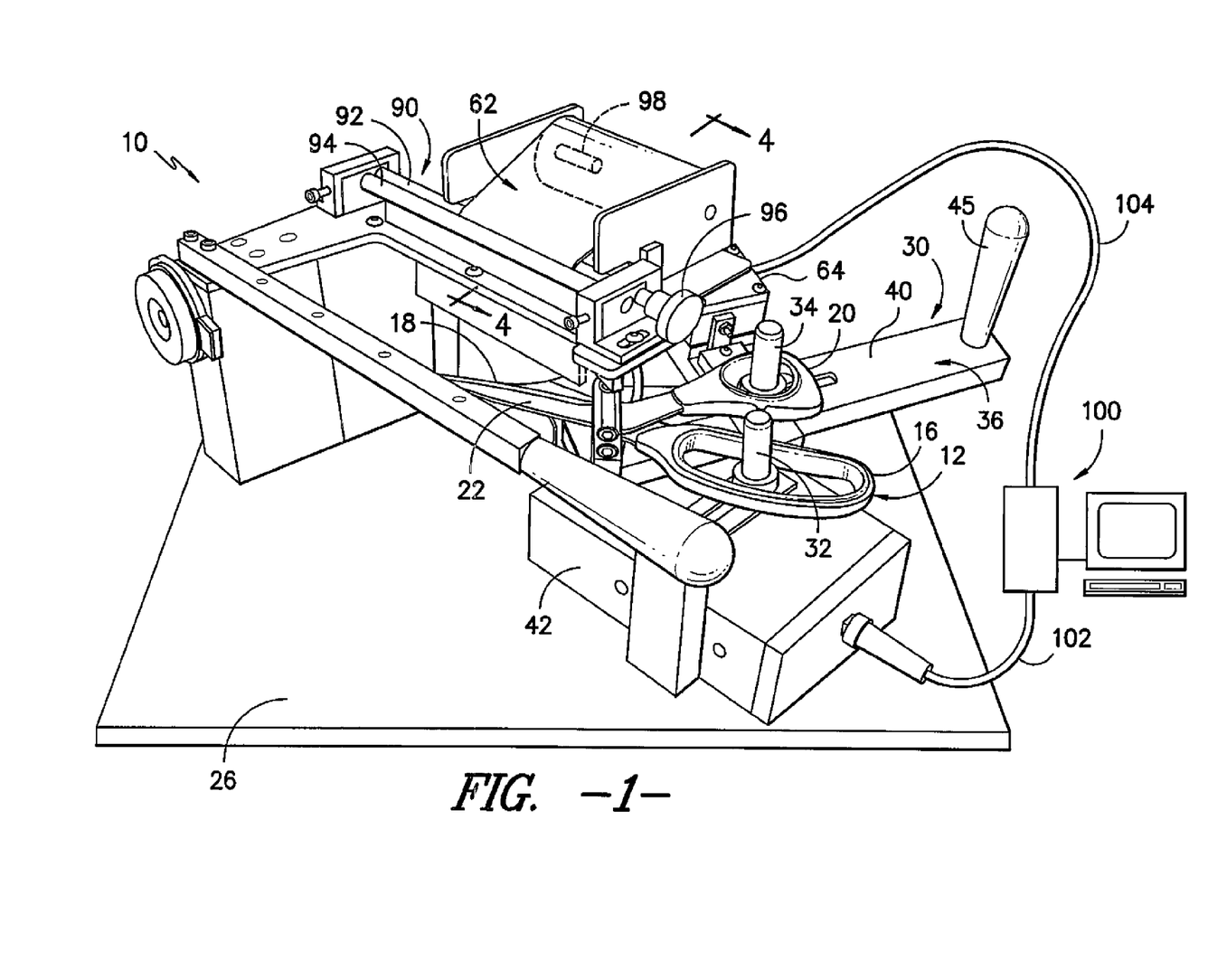
FIG. 1 is a perspective view of a testing device according to one embodiment of the present disclosure.

As shown in FIG. 1, the testing device 10 may include a stand 26. The various other components of the testing device 10 discussed herein, such as the mount device and feed device, may be mounted to the stand 26.

Figure 2:
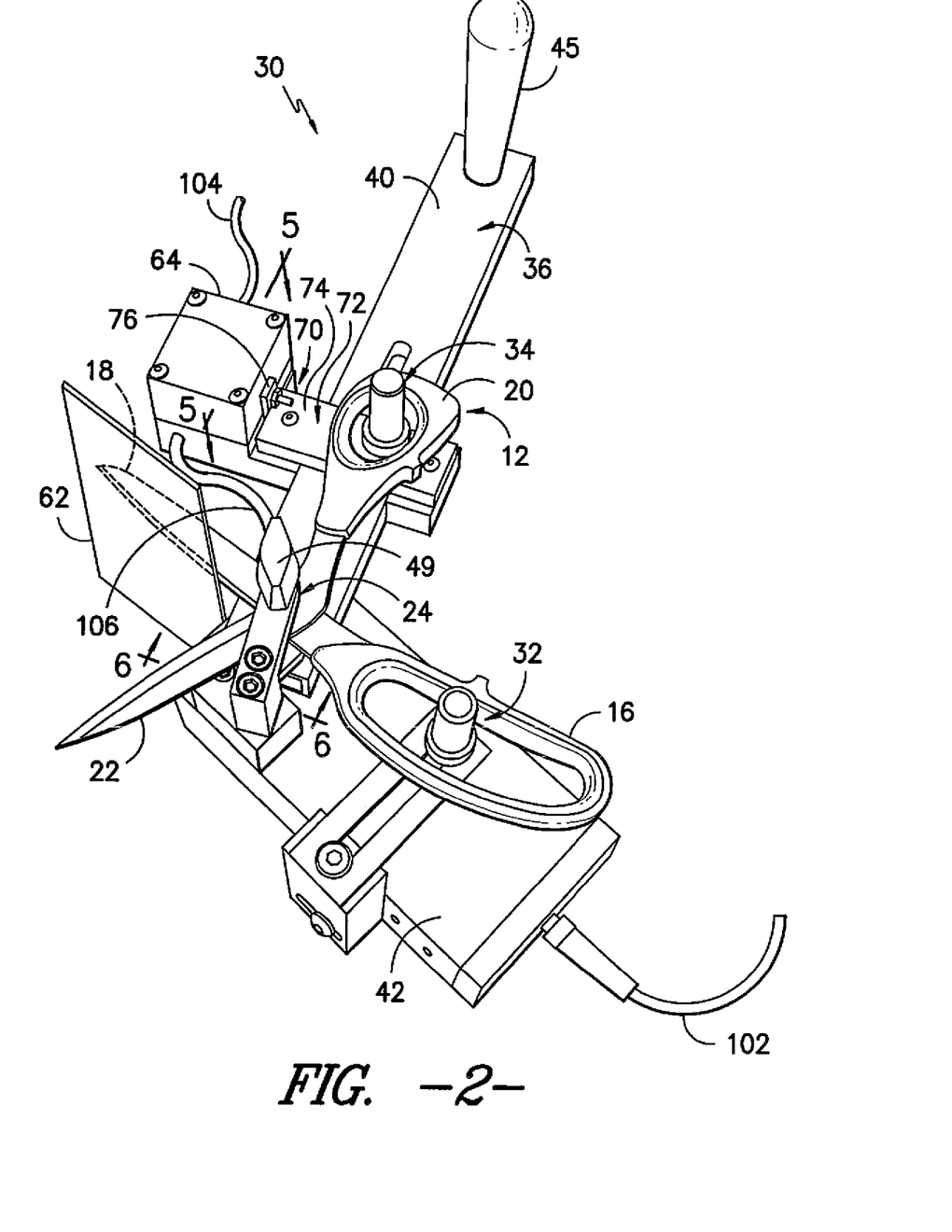
FIG. 2 is a perspective view of a mount device for a testing device in an open position according to one embodiment of the present disclosure.
Figure 3:
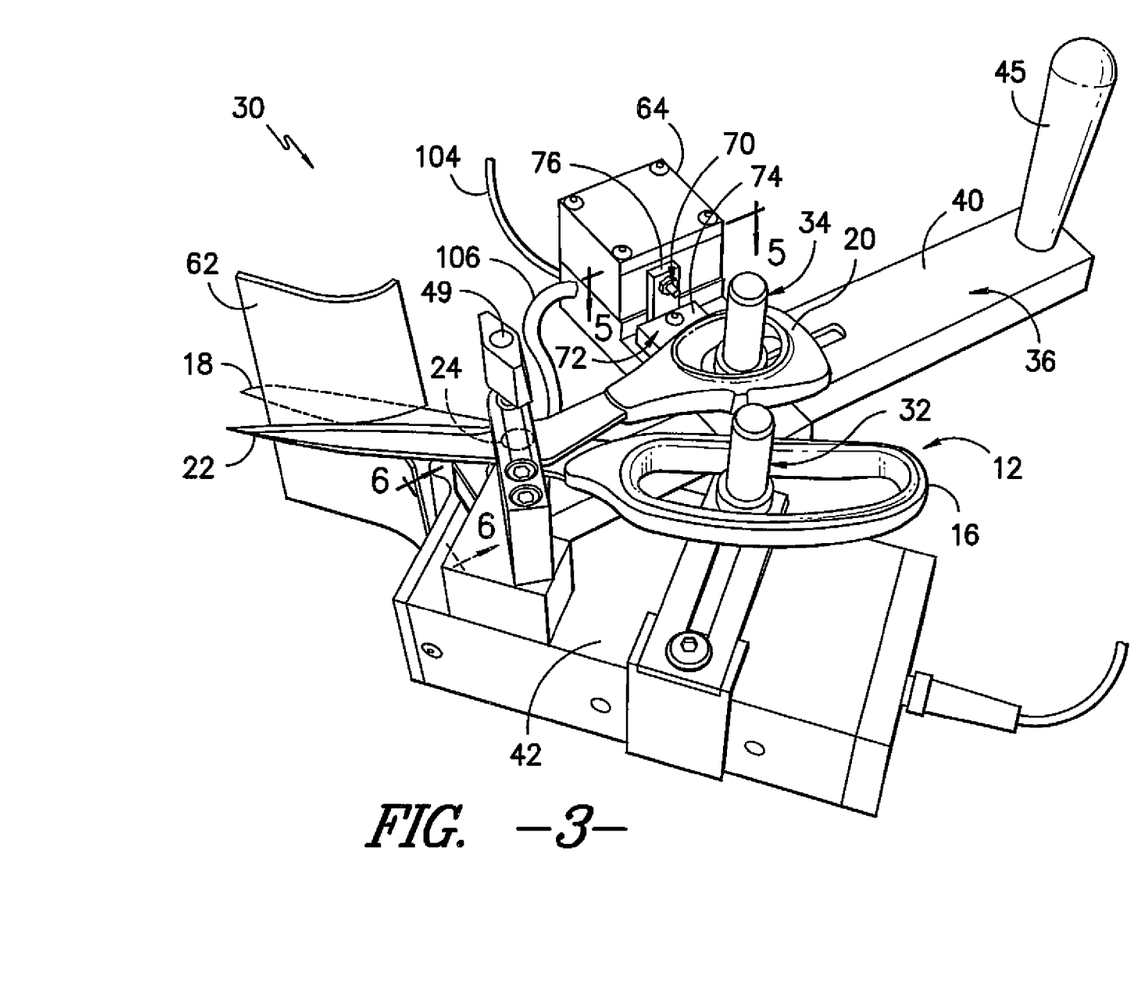
FIG. 3 is a perspective view of a mount device for a testing device moving towards a closed position according to one embodiment of the present disclosure.

As shown in FIGS. 1 through 3, the testing device 10 may include a mount device 30. The mount device 30 may be provided for mounting scissors 12 thereon for testing. For example, a mount device 30 according to the present disclosure includes a first mount feature 32 and a second mount feature 34. The mount features 32, 34 position the scissors for testing. When mounted on the mount features 32, 34, one or both of the grip ends 16, 20 may be allowed to move with respect to the other grip end 16, 20.

The mount features 32, 34 in exemplary embodiments are first and second pins, as shown. In these embodiments, the pins are placed through the respective grip ends 16, 20 of the scissors 12 to mount the scissors 12. In other embodiments, the mount features may be clamps configured to clamp the grip ends 16, 20 therebetween, slots for insertion of the grip ends therein, other suitable protrusions for insertion of the grip ends therethrough, or any other suitable mount features for mounting scissors 12 thereon.

The mount features 32, 34 may be adjustable to fit any suitably sized scissors 12. As shown, in exemplary embodiments, the first mount feature 32 may be disposed in a fixed position. Thus, after adjustment, the first mount feature 32 may be generally fixed such that during testing, generally no movement of the first mount feature 32 occurs. This may thus generally fix the position of the first grip end 16 mounted thereon. Further, the second mount feature 34 may be movable with respect to the first mount feature 32. Thus, after adjustment, the second mount feature 34 may be moved respectively towards and away from the first mount feature 32 to test the scissors 12. This may thus generally move the second grip end 20 with respect to the first grip end 16 to move the scissors between the respective open and closed positions, as shown in respective FIGS. 2 and 3. In exemplary embodiments, the second mount feature 34 may be pivotable with respect to the first mount feature 32, to respectively pivot the second grip end 20 relative to the first grip end 16.

The mount device 30 in exemplary embodiments may further include a swing arm 36. The second mount feature 34 may be disposed on the swing arm 36, and the swing arm 36 may be moved to move the second mount feature 34 and second grip end 20. For example, the swing arm 36 in some embodiments may pivot about a pivot point 38. Thus, second mount feature 34 and second grip end 20 may move along a predetermined arc, which may be adjusted due to adjustment of the second mount feature 34 based on the size of the scissors 12, when the swing arm 36 is pivoted. As shown, the swing arm 36 may include a body 40, on which the second mount feature 34 may be mounted. The pivot point 38 may be disposed at or adjacent to one end of the body 40. For example, the body 40 may be pivotally connected to a housing 42 on which the swing arm 36 is disposed. A rod 44 may pivotally connect the swing arm 36 and housing 42 (see FIG. 6). The swing arm 36 may further include a handle 45 spaced from the pivot point 38. A user of the testing device 10 may grasp the handle 45 to move the swing arm 36 as desired, such as to pivot the swing arm 36. The rod 44 of the swing arm 36 may rotate with respect to the housing 42 to rotate the swing arm 36.

Figure 6:
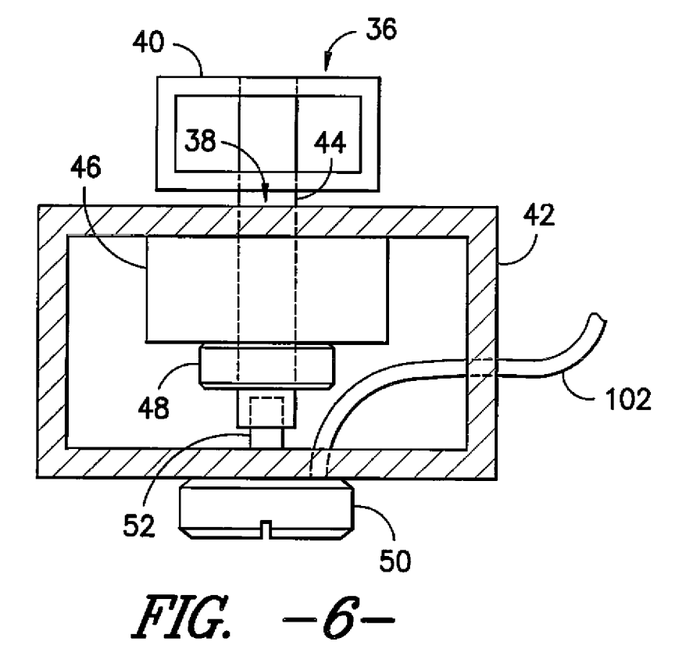
FIG. 6 is a cross-sectional view, along the line 6-6 of FIGS. 2 and 3, of a position sensor for a testing device according to one embodiment of the present disclosure.

As shown in FIG. 6, the rod 44 may extend through the body 40 of the swing arm 36 and through the housing 42 to pivotally connect the swing arm 36 and housing 42. Bearings (not shown) may be provided in the housing 42 surrounding the rod 44 to facilitate rotation of the rod 44. The bearings may be housed in a bearing housing 46 disposed in the housing 42. Further, a bearing preloader 48 may be included, and the rod 44 may further extend through the bearing preloader 48. Set screws (not shown) may couple the rod 44 to the bearing preloader 48.

The mount device 30 in some embodiments may further include a clamp 49. The clamp 49 may, for example, be a screw clamp as shown in FIGS. 2 and 3. The screw clamp 49 may engage the scissors 12, such as at pivot point 24, to further mount the scissors 12 to the mount device 30. This may disposed the pivot point 24 of the scissors 12 in a fixed position, to ensure accurate test results.

A testing device 10 according to the present disclosure may further include a position sensor 50, as shown in FIG. 6. The position sensor 50 may be associated with the mount device 30, and may measure movement of the scissors 12, such as of a moving component thereof. For example, the position sensor 50 in exemplary embodiments may measure movement of the second grip end 20. The position sensor 50 may be connected to or otherwise in communication with the mount device 30 such that movement of the second mount feature 34, and thus movement of the second grip end 20, is detected by the position sensor 50.

In exemplary embodiments as shown, the position sensor 50 is a potentiometer. In other embodiments, the position sensor 50 may be any suitable position sensor, such as any suitable absolute position sensor or relative position sensor, whether linear or angular. Other examples of position sensors include inductive non-contact position sensors, linear variable differential transformers, capacitive transducers, eddy-current sensors, Hall effect sensors, proximity sensors, grating sensors, rotary encoders, seismic displacement pick-ups, piezo-electric transducers, and photodiode arrays.

The position sensor 50 may be associated with the mount device 30. For example, the position sensor 50 may be connected to the second mount feature 34, or to the swing arm 36 or rod 44 thereof as shown in FIG. 6. In exemplary embodiments, the position sensor 50 is connected to the rod 44, which is located at the pivot point 38 and rotates due to movement of the swing arm 36. For example, a rod 52 of the position sensor 50, which may rotate and facilitate measurement of movement by the position sensor 50, may be connected to the rod 44 of the swing arm 36. The rod 52 may extend into the rod 44. Set screws (not shown) may couple the rods 44, 52 together. As the rod rotates 44 due to movement of the swing arm 36, the rod 52 may rotate, and this rotation may be measured by the position sensor 50. Because rotation of the swing arm 36 and second mount feature 34 rotates the second grip end 20, the position sensor 50 thus measures movement, such as rotation, of the second grip end 20.

Figure 5:
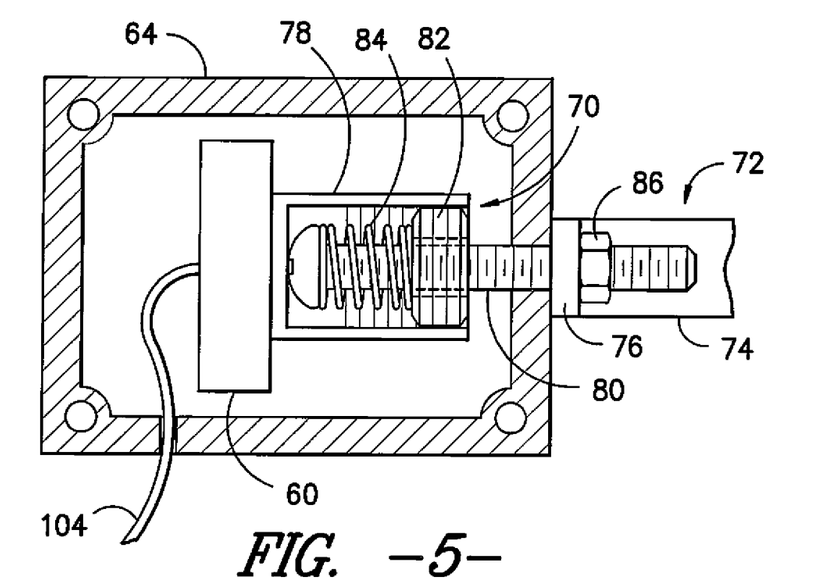
FIG. 5 is a cross-sectional view, along the line 5-5 of FIGS. 2 and 3, of a load sensor and striker device for a testing device according to one embodiment of the present disclosure.

A testing device 10 according to the present disclosure may further include one or more load sensors 60, as shown in FIG. 5. A load sensor 60 according to the present disclosure may be associated with the mount device 30, and may measure loads required for the scissors 12, such as the first blade 18 and second blade 22 thereof, to cut a test media 62 (discussed below). For example, the load sensor 60 in exemplary embodiments may measure pressure and/or force required for the scissors 12 to cut the test media 62. The load sensor 60 may be connected to or otherwise in communication with the mount device 30 such that a load applied to the scissors 12 is detected by the load sensor 60. Load sensor 60 may be housed in a housing 64 as shown, or may be exposed.

In exemplary embodiments as shown, the load sensor 60 is a load cell. The load cell may include one or more strain gauges, or may be hydraulic or hydrostatic, piezoelectric, or vibrating wire load cells. In other embodiments, the load sensor 60 may be any suitable load sensor, such as a suitable pressure sensor.

In exemplary embodiments as shown, a load sensor 60 according to the present disclosure is connected to the second mount feature 34. As the second mount feature 34 is moved to open and close the scissors 12 in order to cut the test media 62, the load utilized to move the second grip end 20 may be transferred to the second mount feature 34. This load may thus be experienced by the second mount feature 34, and thus measured by the connected load sensor 60. Loading of the second grip end 20 may thus be measured. Further, this load measured by loading of the second grip end 20 and second mount feature 34 is the load necessary for the scissors 12, such as the first blade 18 and second blade 22, to cut the test media 62.

In some embodiments, the load sensor 60 may be, for example, in direct contact with the second mount feature 34, such that loading of the second mount feature 34 is directly experienced and measured by the load sensor 60. In other embodiments, as shown in FIG. 5, a striker device 70 may be disposed between the mount device 30 and the load sensor 60, such as between the second mount feature 34 and the load sensor 60. The striker device 70 may transfer the load applied to the mount device 30, such as to the second mount feature 34, to the load sensor 60.

A striker device 70 according to the present disclosure may include, for example, a slider bar 72. The slider bar 72 may be connected to the mount device 30, such as to the second mount feature 34 or to the swing arm 36. In exemplary embodiments, the slider bar 72 is disposed between the second mount feature 34 and swing arm 36, such that the second mount feature 34 is mounted to the swing arm 36 through the slider bar 72. The slider bar 72 may include a body 74 and a flange portion 76 protruding from the body. A striker 78 may be connected to the slider bar 72, such as to the flange portion 76 thereof, by a screw 80 extending through the flange portion 76. A set screw 82 and spring 84 may coupled the striker 78 to the screw 80. A nut 86 may couple the screw 80 to the slider bar 72, such as to the flange portion 76 thereof. The nut 86 and screw 80 may allow for adjustment and calibration of the various components of the striker device 70, and the spring 84 may provide a tension to the striker device 70. The striker 78 may contact the load sensor 60. As the second mount feature 34 is moved, such as by rotation of the swing arm 36, loading applied to the second grip end 20 and thus to the second mount feature 34 and swing arm 36 may be transferred through the striker device 70 to the load sensor 60, which may measure such loading.

In some embodiments, more than one load sensor 60 may be provided. The load sensors 60 may have generally identical or varying ranges and resolutions, such that measurements of loading of the load sensors 60 may be relatively accurate throughout a wide variety of loads, such as throughout a wide variety of forces and/or pressures.

Figure 4:
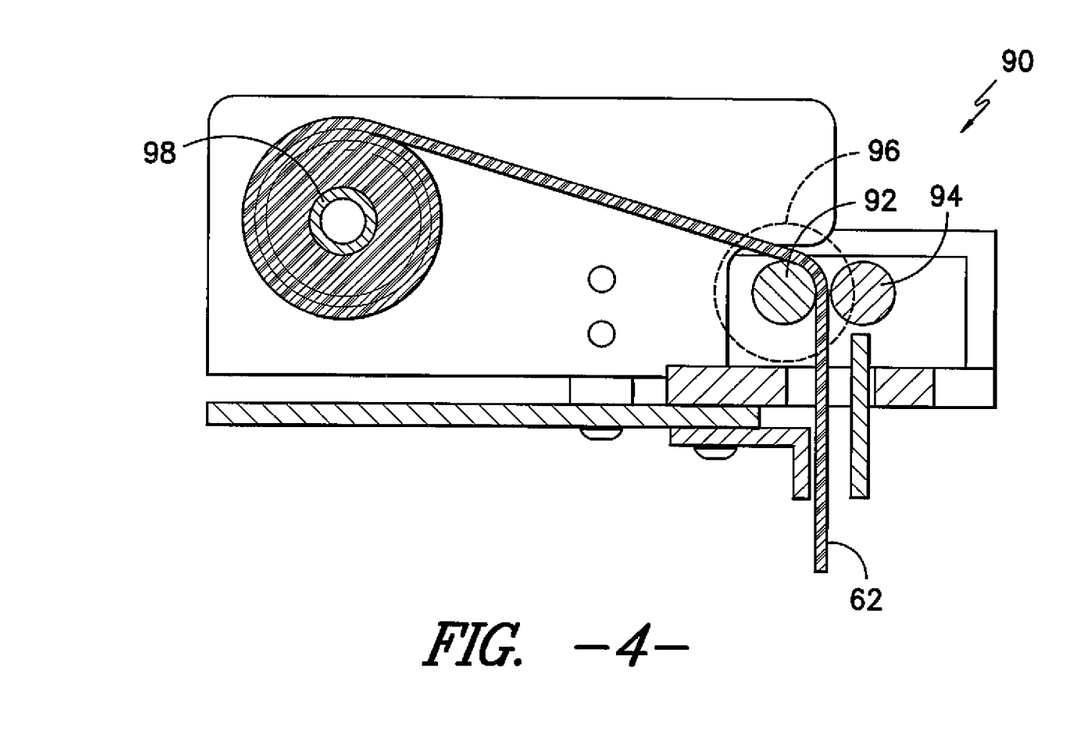
FIG. 4 is a cross-sectional view, along the line 4-4 of FIG. 1, of a feed device for a testing device according to one embodiment of the present disclosure.

A testing device 10 according to the present disclosure may further include a feed device 90, as shown in FIG. 4. The feed device 90 may provide a test media 62 to the scissors 12 for cutting thereof. For example, in exemplary embodiments as shown, the feed device 90 is positioned to provide the test media 62 between the first blade 18 and the second blade 22 of the scissors 12. Test media 62 may thus extend from the feed device 90 to between the first blade 18 and second blade 22. The feed device 90 may advance the test media 62 through the scissors 12 as desired or required such that new test media 62 is available for each cut by the first blade 18 and second blade 22.

In exemplary embodiments, as shown, the feed device 90 includes a first roller 92 and a second roller 94. The first and second rollers 92, 94 may provide the test media 62 therebetween, and this test media 62 may be provided to the scissors. For example, as shown, the rollers 92, 94 may be positioned above the scissors 12, such that test media 62 provided between the rollers 92, 94 may be lowered to between the first blade 18 and second blade 22. One or both of the rollers 92, 94 may include a knob 96, which may be twisted by a user to advance the test media 62 through the rollers 92, 94.

Further, the test media 62 may be held in the testing device on one or more spools 98. The spools 98 may hold one or more rolls of test media 62. The rolls of test media 62 may be provided through the rollers 92, 94 for cutting and testing.

A test media 62 may thus be supplied by the feed device 90 to the scissors 12 for cutting thereof. The test media 62 may be any suitable material for cutting by the scissors 12. For example, the test media 62 may be a rubber, either synthetic or natural, or may be any suitable polymer material. In exemplary embodiments, the test media 62 may be selected based on the similarity of its characteristics to the characteristics of the substance being cut during normal operation by the scissors. For example, in an animal processing application, the test media 62 may be selected based on its similarity to the animal being cut. The normal loading required to cut the test media 62 may thus be similar to the loading required to cut the substance, such as the animal in animal processing applications.

Thus, to test scissors 12 using the testing device 10 of the present disclosure, the scissors 12 may be mounted in the testing device 10 by mounting the scissors 12 to the mount device 30. The scissors 12 in exemplary embodiments may be mounted such that the first grip end 16 is fixed and the second grip end 20 is movable with respect to the first grip end 16, or vice versa, or such that both grip ends 16, 20 are movable, as discussed above. A test media 62 may then be provided to the scissors 12, such as between a first blade 18 and second blade 22 of the scissors 12. The test media 62 may be provided by a feed device 90, as discussed above. The scissors 12 may then be operated to cut the test media 62, such as by moving the scissors 12 from an open position to a closed position. This may, for example, involve moving the second grip end 20 towards the first grip end 16, such as by operating the mount device 30, as discussed above.

During operation of the testing device 10 to test scissors 12, the movement of the scissors 12, such as of the second grip end 20 and/or first grip end 16, as well as the load required for the scissors 12 to cut the test media 62, may be measured. Such measurement may be performed by respective position sensors 50 and load sensors 60. In further exemplary embodiments, a processor 100 may be included in the testing device 10. The processor 100 may be in communication with the position sensors 50 and load sensors 60. Communication between the processor 100 and sensors 50, 60 may be through, for example, wire, fiber optic, and/or wireless transmission such as radio communications. For example, communication to the processor 100 through wire 102 from the position sensor 50 and wire 104 from the load sensor 60 is illustrated in FIGS. 1 through 3, 5, and 6. Further, as shown in FIGS. 2 and 3, a position sensor 50 and load sensor 60 may be in communication, such as through wire 106. The processor 100 may be configured to perform the methods and/or steps described herein. As used herein, the term "processor" is not limited to integrated circuits referred to in the art as a computer, as shown, but broadly refers to a controller, a microcontroller, a microcomputer, a programmable logic controller (PLC), an application specific integrated circuit, and other programmable circuits, and these terms are used interchangeably herein. It should be understood that a processor can also include memory, input channels, and/or output channels.

The processor 100 according to the present disclosure may be in communication with the sensors 50, 60 to be provided with input signals. The input signals received by the processor 100 may be associated with load measurements and provided from a load sensor 60, and/or may be associated with movement measurements and provided from a position sensor 50. Further, additional inputs may be provided to the processor 100. For example, inputs related to the characteristics of the test media 62, and to the size of the scissors 12, may be provided. In one exemplary embodiment, for example, the length of the first blade 18 and second blade 22 may be input into and received by the processor 100.

The processor 100 in exemplary embodiments may be configured to output a correlation between movement of the scissors 12 and loading of the scissors 12 during testing. For example, the processor 100 may output the loading, such as the force, required for the scissors 12 to cut the test media 62. The processor 100 may additionally output the location along the first and second blades 18, 22, where cutting of the test media 62 occurs. Further, the processor 100 may correlate these outputs, so that the loading required is a function of the location along the first and second blades 18, 22 where such cutting, and thus loading, occurred. The location along the first and second blades 18, 22 can be determined based on, for example, the relationship between the movement of the scissors 12 during cutting as measured by the position sensor 50 and the length of the blades 18, 22, because cutting begins at one end of the blades 18, 22, and advances to the other end of the blades 18, 22. Thus, movement of the scissors 12 can be correlated to the length of the blades 18, 22. The processor 100 can perform this correlation, and output location along the length of the blades 18, 22 where cutting is occurring. This location can be correlated with the loading required at that location, as measured by the load sensor 60.

Figure 7:
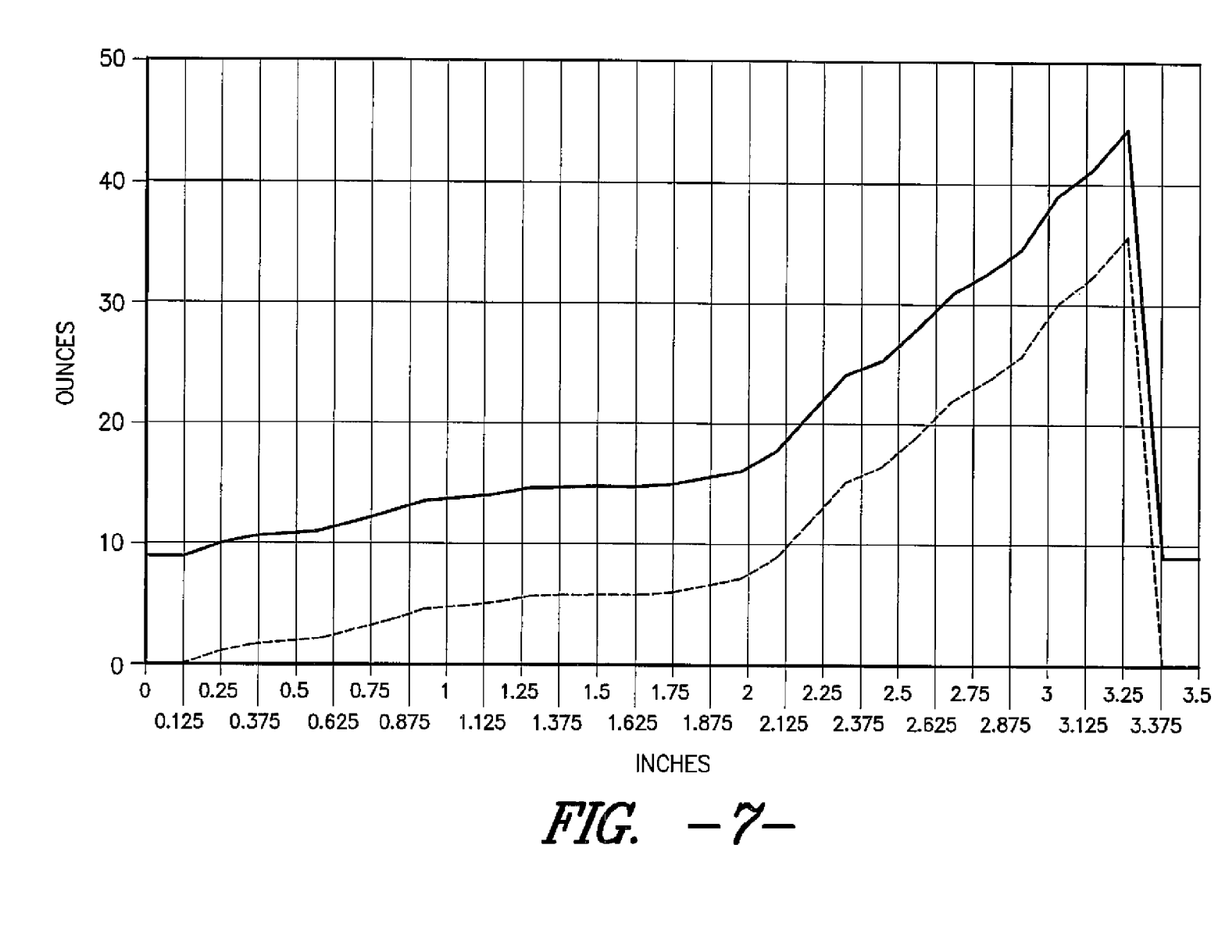
FIG. 7 illustrates the output generated by a testing device according to one embodiment of the present disclosure.

FIG. 7 illustrates one embodiment of the output generated by a testing device 10 and processor 100 thereof according to the present disclosure. The test results for various scissors 12 are shown. Loading, in this embodiment shown as force and measured in ounces, is correlated with blade 18, 22, length, in this embodiment shown as in inches from a base end of the blades 18, 22. Test results utilizing a testing device 10 according to the present disclosure thus advantageously provide not only peak loading information, but also information regarding increases and decreases in loading with respect to blade 18, 22, length and regarding location of peak loading along with respect to blade 18, 22 length.

In some embodiments, a processor 100 according to the present disclosure may further be configured to output a speed at which the scissors 12 cut the test media 62. For example, speed can be determined based on, for example, the relationship between the movement of the scissors 12 during cutting as measured by the position sensor 50 and the length of the blades 18, 22, because cutting begins at one end of the blades 18, 22, and advances to the other end of the blades 18, 22. Thus, movement of the scissors 12 can be correlated to the length of the blades 18, 22. The processor 100 can perform this correlation, and output speed at which cutting is occurring. Speed can be output as an actual speed, or an indication can be output as to whether the speed is in a certain desirable range.

Figure 8:
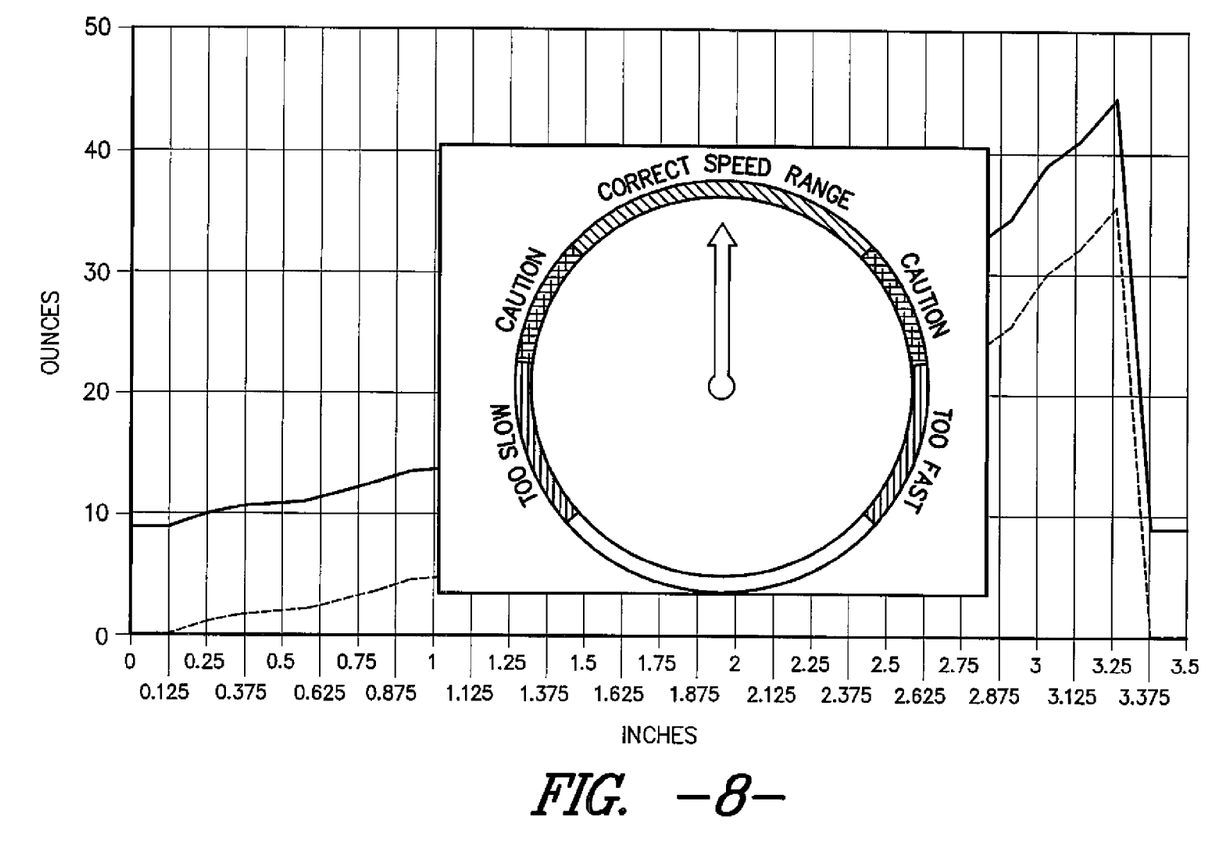
FIG. 8 illustrates the output generated by a testing device according to another embodiment of the present disclosure.

FIG. 8 illustrates another embodiment of the output generated by a testing device 10 and processor 100 thereof according to the present disclosure. The test results for various scissors 12 are shown. Loading is correlated with blade 18, 22 length, similar to FIG. 6. However, in this embodiment, speed at which the scissors 12 cut the test media 62 is additionally output, and displayed as an indication as to whether the speed is in a certain desirable range. Thus, the present testing device 10 further allows for the accuracy of test results to be verified based on confirmation that the testing was performed at appropriate speeds.

The present disclosure is further directed to methods for testing scissors. A method according to the present disclosure may include, for example, receiving a signal associated with a load measurement from a load sensor 60 during cutting of a test media 62 by the scissors 12, and receiving a signal associated with a movement measurement from a position sensor 50 during cutting of the test media by the scissors 12. The method may further include outputting a correlation between load required for the scissors 12 to cut the test media 62 and location along a first blade 18 and second blade 22 of the scissors 12 where cutting of the test media 62 occurs. Additionally, the method may further include outputting a speed at which the scissors 12 cut the test media 62. In exemplary embodiments, the various above disclosed steps are performed through use of a testing device 10, to which the scissors 12 are mounted for testing. In other embodiments, any suitable device or apparatus may be utilized for testing scissors 12 in accordance with the present disclosure.

It should be understood that any one or more of the methods, method steps, and functions discussed herein may be performed automatically or manually. For example, in some embodiments as discussed, various steps required to utilize a testing device 10, such as mounting of scissors 12 and providing of test media 62, may be performed manually. In other embodiments, these steps may be performed automatically. Further, in some embodiments as discussed, other various steps, such as receiving signals and outputting correlations, may be performed automatically, such as automatically by processor 100. In other embodiments, these steps may be performed manually.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A testing device for testing scissors, comprising:
   a mount device, comprising a first mount feature for mounting a first grip end of the scissors thereon and a second mount feature movable with respect to the first mount feature for mounting a second grip end of the scissors thereon;
   a feed device positioned to provide a test media between a first blade and a second blade of the scissors;
   a position sensor associated with the mount device for measuring movement of the second grip end; and
   a load sensor associated with the mount device for measuring a load required for the scissors to cut the test media.

2. The testing device of claim 1, wherein the first mount feature and the second mount feature are first and second pins.

3. The testing device of claim 1, wherein the position sensor is a potentiometer.

4. The testing device of claim 1, wherein the load sensor measures force applied to the second grip end.

5. The testing device of claim 1, wherein the load sensor is a load cell.

6. The testing device of claim 1, wherein the load sensor is connected to the second mount feature.

7. The testing device of claim 1, further comprising a striker device disposed between the mount device and the load sensor, the striker device transferring a force applied to the mount device to the load sensor.

8. The testing device of claim 1, wherein the feed device comprises a first roller and a second roller, the first and second rollers providing the test media therebetween.

9. The testing device of claim 1, wherein the mount device further comprises a swing arm, and wherein the second mount feature is disposed on the swing arm and movable along a predetermined arc.

10. The testing device of claim 9, wherein the position sensor is connected to the swing arm.

11. The testing device of claim 1, further comprising a processor in communication with the position sensor and the load sensor.

12. The testing device of claim 11, wherein the processor is configured to output a correlation between load required for the scissors to cut the test media and location along the first and second blade where cutting of the test media occurs.

13. The testing device of claim 11, wherein the processor is further configured to output a speed at which the scissors cut the test media.

14. A method for testing scissors, comprising:
   receiving a signal associated with a load measurement from a load sensor during cutting of a test media by the scissors;
   receiving a signal associated with a movement measurement from a position sensor during cutting of the test media by the scissors; and
   outputting a correlation between load required for the scissors to cut the test media and location along a first and second blade of the scissors where cutting of the test media occurs.

15. The method of claim 14, further comprising outputting a speed at which the scissors cut the test media.

16. The method of claim 14, further comprising mounting the scissors such that a first grip end of the scissors is generally fixed and a second grip end of the scissors is movable with respect to the first grip end.

17. The method of claim 14, further comprising providing a test media between a first blade and a second blade of the scissors.

18. The method of claim 14, wherein the position sensor measures movement of a second grip end of the scissors.

19. The method of claim 14, wherein the position sensor is a potentiometer.

20. The method of claim 14, wherein the load sensor is a load cell.

* * * * *